United States Patent
Schultz et al.

(10) Patent No.: US 11,529,335 B2
(45) Date of Patent: Dec. 20, 2022

(54) COMPOSITIONS AND METHODS FOR TREATING CANCER

(71) Applicant: UNIVERSITY OF IOWA RESEARCH FOUNDATION, Iowa City, IA (US)

(72) Inventors: Michael K. Schultz, Iowa City, IA (US); Somya Kapoor, Iowa City, IA (US); Douglas R. Spitz, Iowa City, IA (US)

(73) Assignee: UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

(21) Appl. No.: 16/945,323

(22) Filed: Jul. 31, 2020

(65) Prior Publication Data

US 2022/0031674 A1    Feb. 3, 2022

(51) Int. Cl.
| | | |
|---|---|---|
| *A61K 31/437* | (2006.01) | |
| *A61P 35/04* | (2006.01) | |
| *A61K 31/198* | (2006.01) | |
| *A61K 31/4706* | (2006.01) | |
| *A61K 31/66* | (2006.01) | |
| *C07K 16/28* | (2006.01) | |

(52) U.S. Cl.
CPC .......... *A61K 31/437* (2013.01); *A61K 31/198* (2013.01); *A61K 31/4706* (2013.01); *A61K 31/66* (2013.01); *A61P 35/04* (2018.01); *C07K 16/2818* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,658,957 A * | 4/1987 | Guth ..................... | A61J 7/0069 D24/227 |
| 4,820,508 A | 4/1989 | Wortzman | |
| 4,938,949 A | 7/1990 | Borch et al. | |
| 4,992,478 A | 2/1991 | Geria | |
| 5,466,220 A * | 11/1995 | Brenneman ............ | A61J 1/2096 604/87 |
| 6,338,834 B1 | 1/2002 | Jurisson et al. | |
| 6,607,709 B1 | 8/2003 | Jurisson et al. | |
| 6,680,045 B2 | 1/2004 | Jurisson et al. | |
| 7,008,925 B1 | 3/2006 | Szardenings et al. | |
| 7,321,027 B2 | 1/2008 | Mahmood et al. | |
| 7,915,245 B2 | 3/2011 | Srivastava et al. | |
| 8,143,271 B2 | 3/2012 | Ibrahim et al. | |
| 8,986,651 B2 | 3/2015 | Miao et al. | |
| 9,801,922 B2 | 10/2017 | Spitz et al. | |
| 9,980,951 B2 | 5/2018 | Schultz et al. | |
| 10,052,304 B2 | 8/2018 | Allen et al. | |
| 10,729,669 B2 | 8/2020 | Schultz et al. | |
| 2008/0032940 A1 | 2/2008 | Kalyanaraman et al. | |
| 2010/0278845 A1 | 11/2010 | Heavner | |
| 2011/0053938 A1 | 3/2011 | Foley et al. | |
| 2014/0112873 A1 | 4/2014 | Gillies et al. | |
| 2014/0128380 A1 | 5/2014 | Blaskovich et al. | |
| 2015/0038434 A1 | 2/2015 | Yang et al. | |
| 2015/0119341 A1 | 4/2015 | Yang et al. | |
| 2015/0284431 A1 | 10/2015 | Cai et al. | |
| 2016/0046688 A1 | 2/2016 | Perricone et al. | |
| 2016/0136309 A1 | 5/2016 | Rosch et al. | |
| 2018/0214402 A1 | 8/2018 | Schultz et al. | |
| 2019/0321495 A1 | 10/2019 | Schultz et al. | |
| 2020/0054635 A1 * | 2/2020 | Campbell .......... | A61K 31/4375 |
| 2020/0147060 A1 * | 5/2020 | Schultz .................. | A61P 35/00 |
| 2021/0113503 A1 * | 4/2021 | Schultz .............. | A61K 39/3955 |

FOREIGN PATENT DOCUMENTS

| | | | |
|---|---|---|---|
| CN | 104974745 A | 10/2015 | |
| EP | 1574213 A1 | 9/2005 | |
| EP | 1847274 A1 | 10/2007 | |
| EP | 2036990 A1 * | 3/2009 | .......... C12Q 1/6886 |
| EP | 2698156 A1 | 2/2014 | |
| GB | 2185486 A | 7/1987 | |
| WO | 1990003798 A2 | 4/1990 | |
| WO | 1993015733 A1 | 8/1993 | |
| WO | 1993021963 A2 | 11/1993 | |
| WO | 2005023179 A2 | 3/2005 | |
| WO | 2009151708 A2 | 12/2009 | |
| WO | 2010129248 A1 | 11/2010 | |
| WO | 2011063366 A1 | 5/2011 | |
| WO | 2011063367 A1 | 5/2011 | |
| WO | 2013019975 A1 | 2/2013 | |

(Continued)

OTHER PUBLICATIONS

Defty et al., "Melphalan in Regional Chemotherapy for Locally Recurrent Metastatic Melanoma", 2012, Current Topics in Medicinal Chemistry, vol. 12, No. 1, pp. 53-60. (doi: 10.2174156802612798919187) (Year: 2012).*

Khamari et al., "Glucose metabolism and NRF2 coordinate the antioxidant response in melanoma resistant to MAPK inhibitors", 2018, Cell Death and Disease, 9(325), pp. 1-14. (doi:http://dx.doi.org/10.1038/s41419-018-0340-4) (Year: 2018).*

Xiao et al., "Glutathione Metabolism in Renal Cell Carcinoma Progression and Implications for Therapies", 2019, Int. J. Mol. Sci., 20 (15), Article:3672, pp. 1-20. (doi: 10.3390/ijms20153672) (Year: 2019).*

Patent Cooperation Treaty , International Searrching Authority, Search Report and Written Opinion for PCT/US17/039299, 9 pages, dated Sep. 14, 2017.

(Continued)

*Primary Examiner* — My-Chau T. Tran
(74) *Attorney, Agent, or Firm* — Viksnins Harris Padys Malen LLP

(57) ABSTRACT

The invention provides compositions and methods to treat a hyperproliferative disorder with a GSH synthesis inhibitor and an anti-cancer composition.

14 Claims, 6 Drawing Sheets

(6 of 6 Drawing Sheet(s) Filed in Color)

(56) References Cited

FOREIGN PATENT DOCUMENTS

| WO | 2014072493 | A1 |   | 5/2014 |   |            |
|----|------------|----|---|--------|---|------------|
| WO | 2014124384 | A1 |   | 8/2014 |   |            |
| WO | WO-2016168150 | A2 | * | 10/2016 | ........... | A61K 31/713 |
| WO | WO-2021168283 | A1 | * | 8/2021  | ............. | A61K 31/00 |

OTHER PUBLICATIONS

Phillips, J , et al., "Pilot study of sodium phenylbutyrate as adjuvant in cyclophosphamide-resistant endemic Burkitt's lymphoma", Transaction of the Royal Society of Tropical Medicine and Hygiene 101, 1265-1269 (2007).

Puck, T , et al., "Action of x-rays on mammalian cells. II. Survival curves of cells from normal human tissues", J Exp Med 106, 485-500 (1957).

Raposinho, P , et al., "Melanoma targeting with alpha-melanocyte stimulating hormone analogs labeled with fac-[99mTc(CO)3]+ effect of cyclization on tumor-seeking properties", J Biol Inorg Chem 13, 449-459 (2008).

Reedy, J , et al., "Synthesis and Evaluation of Tetraarylethylene-based Mono-, Bis-, and Tris(pyridinium) Derivatives for Image-Guided Mitochondria-Specific Targeting and Cytotoxicity of Metastatic Melanoma Cells", Bioconjugate Chem 27, 2424-2430 (2016).

Ripcke, J , et al., "Small-molecule targeting of the mitochondrial compartment with an endogenously cleaved reversible tag", ChemBioChem 10(10), 1689-1696 (2009).

Rohlena, J , et al., "Anticancer drugs targeting the mitochondrial electron transport chain", Antioxid. Redox Signaling 15(12), 2951-2974 (2011).

Schibler, J , et al., "Mitochondrial-Targeted DecylTriphenylphosphonium Enhances 2-Deoxy-D-Glucose Mediated Oxidative Stress and Clonogenic Killing of Multiple Myeloma Cells", PLOS One 11(11): e0167323 (2016).

Schniewind, B , et al., "Combination phenylbutyrate/gemcitabine therapy effectively inhibits in vitro and in vivo growth of NSCLC by intrinsic apoptotic pathways", Journal of Carcinogenesis 5(25), 11 pages (2006).

Simons, A., et al., "Glucose deprivation-induced metabolic oxidative stress and cancer therapy", J. Cancer Res. Ther. 5(Suppl 1) S2, 7 pages (2009).

Simons, A, et al., "Inhibition of glutathione and thioredoxin metabolism enhances sensitivity to perifosine in head and neck cancer cells", J Oncol 2009, 519563, 10 pages (2009).

Smith, R , et al., "Animal and human studies with the targeted antioxidant MitoQ", Annals of the New York Academy of Sciences 1201, 96-103 (2010).

Smith, R., et al., "Delivery of Bioactive Molecules to Mitochondria in vivo", PNAS, vol. 100, No. 9, 5407-5412 (2003).

Sousa, R , et al., "Treatment for metastatic melanoma: a new and evolving era", Int J Clin Pract 69(3), 273-280 (2015).

Spitz, D , et al., "Cytotoxicity and metabolism of 4-hydroxy-2-nonenal and 2-nonenal in H2O2-resistant cell lines. Do aldehydic by-products of lipid peroxidation contribute to oxidative stress?", Biochem J 267, 453-459 (1990).

Spitz, D , et al., "Glucose deprivation-induced oxidative stress in human tumor cells. A fundamental defect in metabolism?", Ann. N. Y. Acad. Sci., 899, 349-362 (2000).

Tolk, H , et al., "Complete remission of metastatic melanoma upon BRAF inhibitor treatment—what happens after discontinuation?", Melanoma Res 25(4), 362-366 (2015).

Tong, H , et al., "Fluorescent "light-up" bioprobes based on tetraphenylethylene derivatives with aggregation-induced amission characteristics", Chem Commun 35, 3705-3707 (2006).

Trnka, J , et al., "Lipophilic triphenylphosphonium cations inhibit mitochondrial electron transport chain and induce mitochondrial proton leak", PLoS One 10(4), e0121837, 14 pages (2015).

Tseng, W , et al., "Long-term survivors after immunotherapy for metastatic melanoma", Immunol Lett 139(1-2), 117-118 (2011).

Wang, Z , et al., "Long-term fluorescent cellular tracing by the aggregates of AIE bioconjugates", J. Am. Chem. Soc. 135(22), 8238-8245 (2013).

Wunderlin, R , et al., "Melanotropin Receptors II. Synthesis and Biological Activity of alpha-Melanotropin/Tobacco Mosaic Virus Disulfide Conjugates", Helvetica Chimica Acta 68, 12-22 (1985).

Yong, K , et al., "Towards translation of 212Pb as a clinical therapeutic; getting the lead in!", Dalton Trans 40, 6068-6076 (2011).

Yuan, H , et al., "Fluorescent and radiolabeled triphenylphosphonium probes for imaging mitochondria", Chem. Commun. 49 (88), 10361-10363 (2013).

Zain, J. , et al., "Targeting Histone Deacetyalsa in the Treatment of B-and T-cell Malignancies", Invest New Drugs 28 (Suppl 1), S58-S78 (2010).

Zhang, G , et al., "General Synthetic Approach toward Geminal-Substituted Tetraalylethene Fluorophores with Tunable Emission Properties: X-ray Crystallography, Aggregation-Induced Emission and Piezofluorochromism", Chemistiy Materials 26(15), 4433-4446 (2014).

Ackerman, A , et al., "Outcomes of patients with metastatic melanoma treated with immunotherapy prior to or after BRAF inhibitors", Cancer 120(11), 1695-1701 (2014).

Adekola, K , et al., "Glucose transporters in cancer metabolism", Curr. Opin. Oncol. 24(6), 650-654 (2012).

Ahmad, I, et al., "Mitochondrial O2*- and H2O2 mediate glucose deprivation-induced stress in human cancer cells", J Biol Chem 280, 4254-4263 (2005).

Asundi, J , et al., "MAPK Pathway Inhibition Enhances the Efficacy of an Anti-Endothelin B Receptor Drug Conjugate by Inducing Target Expression in Melanoma", Mol Cancer Ther 13 (6), 1599-1610 (2014).

Aykin-Burns , et al., "Increased levels of superoxide and H2O2 mediate the differential susceptibility of cancer cells versus normal cells to glucose deprivation", Biochem J, 418(1), 29-37 (2009).

Beaino, W , et al., "PET Imaging of Very Late Antigen-4 in Melanoma: Comparison of 68Ga- and 64Cu-Labeled NODAGA and CB-TE1A1P-LLP2A Conjugates", J Nucl Med 55, 1856-1863 (2014).

Birch-Machin, M , et al., "An evaluation of the measurement of the activities of complexes I-IV in the respiratory chain of human skeletal muscle mitochondria", Biochem Med Metab Biol 51(1), 35-42 (1994).

Bradford, M , et al., "A rapid and sensitive method for the quantitation of microgram quantities of protein utilizing the principle of protein-dye binding", Anal Biochem 72, 248-254 (1976).

Burkitt, K , et al., "Phenylbutyrate interferes with the Fanconi anemia and BRCA pathway and sensitizes head and neck cancer cells to cisplatin", Molecular Cancer 7(24), 9 pages (2008).

Cecil Textbook of Medicine , Cecil Textbook of Medicine, 20th Edition, vol. 1 (1996).

Chen , "Mitochondrial membrane potential in living cells", Ann Rev Cell Biol 4, 155-181 (1988).

Dai, J., et al., "Malignant Cells Can be Sensitized to Undergo Growth Inhibition and Apoptosis by Arsenic Trioxide Through Modulation of the Glutathione Redox System", Blood, vol. 93, No. 1, 268-277 (1999).

Ding, D , et al., "Bioprobes based on AIE fluorogens", Acc. Chem. Res. 46(11), 2441-2453 (2013).

Fath, M , et al., "Enhancement of carboplatin-mediated lung cancer cell killing by simultaneous disruption of glutathione and thioredoxin metabolism", Clin Cancer Res 17 (19), 6206-6217 (2011).

Fath, M , et al., "Mitochondrial electron transport chain blockers enhance 2-deoxy-D-glucose induced oxidative stress and cell killing in human colon carcinoma cells", Cancer Biol Ther 8(13), 1228-1236 (2009).

Figg, W , et al., "In vitro antitumor effect of hydroxyurea on hormone-refractory prostate cancer cells and its potentiation by phenylbutyrate", Anti-Cancer Drugs 5, 336-342 (1994).

Froidevaux, S , et al., "A Novel DOTA-cx-Melanocyte-Stimulating Hormone Analog for Metastatic Melanoma Diagnosis", J Nucl Med 43, 1699-1706 (2002).

(56) References Cited

OTHER PUBLICATIONS

Gabr, M , et al., "Synthesis and aggregation-induced emission properties of pyridine and pyridinium analogues of tetraphenylethylene", RSC Adv 5, 90226-90234 (2015).
Gius, D , et al., "Redox signaling in cancer biology", Antioxid Redox Signal 8(7-8), 1249-1252 (2006).
Goodall, M , et al., "Development of potent autophagy inhibitors that sensitize oncogenic BRAF V600E mutant melanoma tumor cells to vemurafenib", Autophagy 10(6), 1120-1136 (2014).
Gore, S , "In vitro basis for treatment with hypomethylating agents and histone deacetylase inhibitors: can epigenetic changes be used to monitor treatment?", Leukemia Research 33 Suppl 2, S2-S6 (2009).
Griffith, O , et al., "Determination of glutathione and glutathione disulfide using glutathione reductase and 2-vinylpyridine", Anal Biochem 106, 207-212 (1980).
Guo, H , et al., "Reduction of the Ring Size of Radiolabeled Lactam Bridge-Cyclized a-MSH Peptide, Resulting in Enhanced Melanoma Uptake", J Nucl Med 51, 418-426 (2010).
Gura, "Systems for Identifying New Drugs are Often Faulty", Science 278 (5340), 1041-1042 (1997).
Han, H , et al., "The rational design of a gemcitabine prodrug with AIE-based intracellular light-up characteristics for selective suppression of pancreatic cancer cells", Chem Commun (Camb). 51(98):17435-17438 (2015).
Howlader, N , et al., "SEER Cancer Statistics Review, 1975-2014", National Cancer Institute. Bethesda, MD, https://seer.cancer.gov/csr/1975_2014/, based on Nov. 2016 SEER data submission, posted to the SEER website, Apr. 2017.
Hu, Q , et al., "Mitochondria-targeted cancer therapy using a light-up probe with aggregation-induced-emission characteristics", Angew. Chem. Int. Ed. Engl. 53(51), 14225-14229 (2014).
Indran, I, et al., "Recent advances in apoptosis, mitochondria and drug resistance in cancer cells", Biochim. Biophys. Acta 1807(6), 735-745 (2011).
Johnson, J , et al., "Relationships between drug activity in NCI preclinical in vitro and in vivo models and early clinical trials", British J of Cancer 84, 1424-1431 (2001).
Jordan, E , et al., "Vemurafenib for the treatment of melanoma", Expert Opinion on Pharmacotherapy 13(17), 2533-2543 (2012).
Lai, F , et al., "Histone Deacetylases (HDACs) as Mediators of Resistance to Apoptosis in Melanoma and as Targets for Combination Therapy with Selective BRAF Inhibitors", Advances in Pharmacology 65, ISSN 1054-3589, 27-43 (2012).
Lee, A, "GRP78 induction in cancer: therapeutic and prognostic implications", Cancer Res 67, 3496-3499 (2007).
Leung, C , et al., "A photostable AIE luminogen for specific mitochondrial imaging and tracking", J. Am. Chem. Soc. 135(1), 62-65 (2013).
Lin, X , et al., "2-Deoxy-D-glucose-induced cytotoxicity and radiosensitization in tumor cells is mediated via disruptions in thiol metabolism", Cancer Res. 63 (12), 3413-3417 (2003).
Little, A, et al., "A New Combination Therapy for Metastatic Melanoma", University of Iowa Summer Undergraduate Research Day, University of Iowa, Iowa City, IA (2015).
Liu , et al., "A Small-Molecule Inhibitor of Glucose Transporter 1 Downregulates Glycolysis, Induces Cell-Cycle Arrest, and Inhibits Cancer Cell Growth In Vitro and In Vivo", Molecular Cancer Therapy, 11(8), 1672-1682 (2012).
Lowry, O , "Protein measurement with the Folin phenol reagent", J Biol Chem 193(1), 265-275 (1951).
Malo, A, et al., "4-Phenylbutyric acid reduces endoplasmic reticulum stress, trypsin activation, and acinar cell apoptosis while increasing secretion in rat pancreatic acini", Pancreas 42, 92-101 (2013).
Manic, G , et al., "Chloroquine and hydroxychloroquine for cancer therapy", Mol Cell Oncol 1(1), e29911, doi:10.4161/mco.29911, 11 pages (2014).
Martin, M , et al., ""Click" cyclized gallium-68 labeled peptides for molecular imaging and therapy: Synthesis and preliminary in vitro and in vivo evaluation in a melanoma model system", Recent Results Cancer Res 194, 149-175 (2013).
Millard, Melissa , et al., "Preclinical Evaluation of Novel Triphenylphosphonium Salts with Broad-Spectrum Activity", PLoS One vol. 5 (10), e13131, 1-18 (2010).
Misra, UK, et al., "The role of Grp 78 in alpha 2-macroglobulin-induced signal transduction. Evidence from RNA interference that the low density lipoprotein receptor-related protein is associated with, but not necessary for, GRP 78-mediated signal transduction", J Biol Chem. 277(44), 42082-42087 (2002).
Modica-Napolitano, J , et al., "Delocalized lipophilic cations selectively target the mitochondria of carcinoma Dells", Adv. Drug Delivery Rev. 49(1-2), 63-70 (2001).
Mueckler, M , "Facilitative glucose transporters", Eur. J. Biochem. 219(3), 713-725 (1994).
Murphy, M , et al., "Drug delivery to mitochondria: the key to mitochondrial medicine", Adv. Drug Delivery Rev. 41(2), 235-250 (2000).
Murphy, M , "Flow mitochondria produce reactive oxygen species", Biochem J 417(1), 1-13 (2009).
Murphy, M , et al., "Targeting antioxidants to mitochondria by conjugation to lipophilic cations", Annu. Rev. Pharmacol. Toxicol. 47, 629-656 (2007).
Murphy, M , "Targeting lipophilic cations to mitochondria", Biochim. Biophys. Acta 1777 (7-8), 1028-1031 (2008).
O'Dwyer, P. , et al., "Phase 1 Trial of Buthionine Sulfoximine in Combination with Melphalan in Patients with Cancer" Oncol. vol. 14, No. 1, 249-256 (1996).
Patent Cooperation Treaty , International Searching Authority, Search Report and Written Opinion for PCT/US2016/43993, 13 pages, dated Oct. 4, 2016.
Kapoor, S , et al., "MAPK-pathway inhibition driven changes in cellular thiol-redox state mediate drug resistance in metastatic melanoma", Pigment Cell and Melanoma Research vol. 33 (1), 1 page (2020).
Patent Cooperation Treaty , International Searching Authority, Search Report and Written Opinion for PCT/US2021/041958, 12 pages, dated Oct. 29, 2021.

* cited by examiner

COMPOSITIONS AND METHODS FOR TREATING CANCER

STATEMENT REGARDING FEDERALLY SPONSORED RESEARCH

This invention was made with government support under CA172218 awarded by the National Institutes of Health and 2012-DN-130-NF0001 awarded by the Department of Homeland Security. The government has certain rights in the invention.

BACKGROUND

Melanoma is a cancer of the skin and is the fastest growing cancer incidence in the world today. Disease detected early can be removed by surgery, but when melanoma spreads to other parts of the body (called metastatic melanoma) it is almost uniformly fatal. The reason for this is that metastatic melanoma rapidly becomes resistance to all forms of treatment. The first new therapy that appeared effective for melanoma was approved in 2011. The pharmaceutical called vemurafenib targets patients with a gene mutation ($BRAF^{V600E}$) that is present in about half of melanoma patients. Although these patients respond well to the treatment, melanoma develops resistance to the therapy rapidly. Thus, the new therapy, which initially was heralded as the end of melanoma, extends life expectancy by only months with severe side effects. Vemurafenib is one of several BRAF inhibitors that are being used for melanoma therapy that target the BRAF protein. Melanoma develops resistance to all of these therapies. Several other drugs that have different mechanisms of action are also approved for melanoma treatment, but the disease eventually develops resistance to all therapies for melanoma. There is no treatment for metastatic melanoma that overcomes resistance of melanoma cancer cells, which leads to a high mortality rate.

Small molecule MAPK inhibitors (MAPKi, e.g. BRAFI: vemurafenib, dabrafenib and MEKi: cobimetinib, tramatinib) have been shown to significantly reduce tumor burden, and often delay disease progression. However, resistance to MAPKi is observed (almost invariably) within 6-8 months, which limits the overall clinical outcomes for patients undergoing MAPKi therapies. The precise cellular mechanism that drives MAPKi resistance in metastatic melanoma is not known. However, evidence suggests several plausible mechanisms, including re-activation of the MAPK pathway; metabolic re-programming; and stress-induced adaptive responses (e.g., autophagy and unfolded protein response). Unfortunately, therapeutic strategies targeting these mechanisms to circumvent the development of MAPKi resistance have yet to yield significant improvement in clinical outcomes for metastatic melanoma patients.

There is therefore a need for compositions and methods for the treatment of melanoma that prevents melanoma tumors from acquiring resistance to MAPKi.

SUMMARY

In certain embodiments, the present invention provides the use of a glutathione (GSH) synthesis inhibitor in conjunction with one or more anti-cancer compositions for the therapeutic treatment of a hyperproliferative disorder. The use of the GSH synthesis inhibitor is effective in preventing drug resistance in the treatment of metastatic melanoma or other types of cancer cells.

In certain embodiments, the hyperproliferative disorder is cancer. In certain embodiments, the cancer is drug-resistant. As used herein, the term "drug-resistant" is reduction in effectiveness of a drug in killing malignant cells; reducing cancerous tumor size and rate of growth; and ameliorating the disease or condition. In certain embodiments, the drug's effectiveness is reduced by at least about 10%, 20%, 30%, 40%, 50%, 60%, 70%, 80%, 90%, or even 100%, as compared to its effects when first administered to the mammal.

In certain embodiments, the cancer is melanoma. In certain embodiments, the melanoma is resistant to MAPK pathway inhibitors. In certain embodiments, the melanoma is resistant to vemurafenib treatment.

In certain embodiments, a phenyl butyric acid (PBA) or a pharmaceutically acceptable salt thereof is administered simultaneously with the anti-cancer composition.

In certain embodiments, the GSH synthesis inhibitor and the anti-cancer composition are administered sequentially.

In certain embodiments, the administration of the GSH synthesis inhibitor begins about 1 to about 10 days before administration of the anti-cancer composition.

In certain embodiments, the administration of the GSH synthesis inhibitor and administration of the anti-cancer composition begins on the same day and/or simultaneously.

In certain embodiments, the GSH synthesis inhibitor is buthionine sulfoximine (BSO).

In certain embodiments, the anti-cancer composition comprises vemurafenib.

In certain embodiments, the anti-cancer composition comprises chloroquine (or hydroxychloroquine). In certain embodiments, the anti-cancer composition comprises a derivative of triphenylphosphonium (TPP), or a pharmaceutically acceptable salt thereof.

In certain embodiments, the anti-cancer composition comprises is ipilimumab.

In certain embodiments, the PBA or a pharmaceutically acceptable salt thereof is administered in combination with vemurafenib, and the cancer is melanoma.

In certain embodiments, the PBA or a pharmaceutically acceptable salt thereof is administered in combination with vemurafenib and chloroquine (or hydroxychloroquine), and the cancer is melanoma.

In certain embodiments, the present invention provides a use of the combination of a GSH synthesis inhibitor and anti-cancer composition in the preparation of a medicament for the treatment of a hyperproliferative disorder in a mammal.

In certain embodiments, the present invention provides a kit comprising a GSH synthesis inhibitor, a container, and a package insert or label indicating the administration of the GSH synthesis inhibitor with an anti-cancer composition for treating a hyperproliferative disorder.

In certain embodiments, the present invention provides a product comprising a GSH synthesis inhibitor and an anti-cancer composition; as a combined preparation for separate, simultaneous or sequential use in the treatment of a hyperproliferative disorder.

In certain embodiments, the present invention provides a method for treating a hyperproliferative disorder in a mammal, comprising administering to the mammal a combination of a GSH synthesis inhibitor; and an anti-cancer composition.

In certain embodiments, the GSH synthesis inhibitor is administered for more than a month.

In certain embodiments, the GSH synthesis inhibitor is administered for more than a year.

In certain embodiments, the GSH synthesis inhibitor or a pharmaceutically acceptable salt thereof is administered at a dosage of at least 0.1/mg/kg/day.

In certain embodiments, the GSH synthesis inhibitor is administered at a dosage of at least 100 mg/kg/day.

In certain embodiments, the present invention provides a use of a GSH synthesis inhibitor and an anti-cancer composition for the therapeutic treatment of a hyperproliferative disorder. In certain embodiments, the hyperproliferative disorder is cancer. In certain embodiments, the cancer is melanoma.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
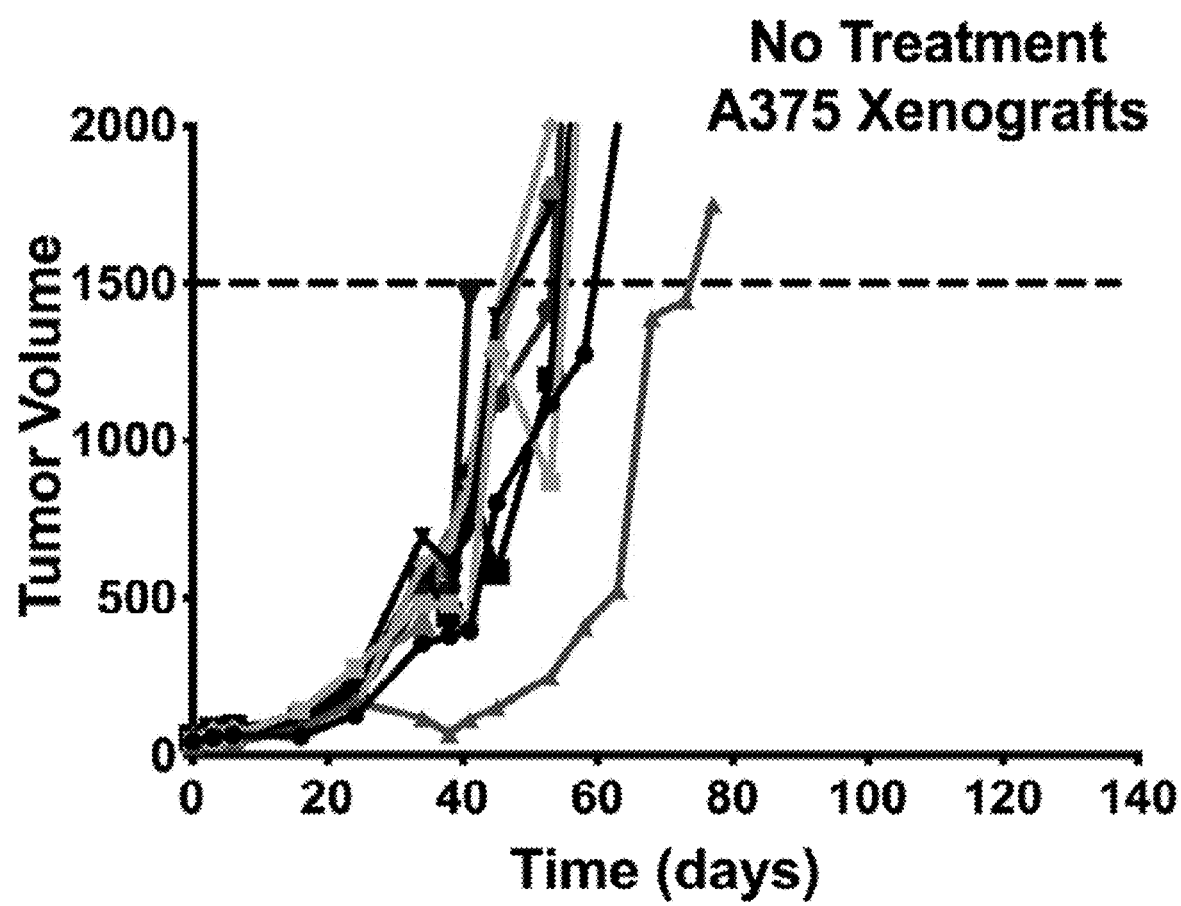
FIG. 1(a)-1(b) are graphs illustrating no significant difference in tumor growth rate for untreated controls (FIG. 1(a)) and mice treated with BSO alone (FIG. 1(b)).

Melanoma is the dangerous type of skin cancer that develops in cells that produce melanin (melanocytes), usually presenting as an irregular spot/mole on the skin. Causes of melanoma include UV radiation and a genetic predisposition to this type of cancer. Unlike other cancers, prevalence of melanoma is increasing, with the highest occurrence among individuals 25-29 years old. The overall lifetime risk of developing melanoma is 2.4%. In 2015, 73,870 new invasive melanomas are expected to be diagnosed, with 9,940 people expected to die of melanoma. With early treatment, survival rate is 97%.

Melanoma can migrate to other parts of the body (metastatic melanoma), and one-year survival rate drastically decreases with metastasis—15-20% for Stage IV. Current types of treatment include surgery, immunotherapy (Immune checkpoint inhibitors for advanced melanoma), chemotherapy, radiation therapy, targeted therapy (target cells with gene changes) and BRAF Inhibitors. BRAF is a protein kinase of the mitogen-activated protein kinase (MAPK) pathway, and it regulates cell growth, proliferation, and differentiation. Research suggests a BRAF$^{V600E}$ mutation causes the BRAF protein (produced through the MAPK pathway) to become oncogenic. The mutation may lead to increased and uncontrolled cell proliferation, and resistance to apoptosis. The BRAF mutation is observed in about 50% of melanoma tumors. Its presence is associated with poor prognosis in metastatic melanoma.

Melanoma is the fastest growing cancer incidence in the United States. Surgery is curative for melanoma confined to the skin, but metastatic melanoma is lethal. Current FDA approved therapies for metastatic melanoma (e.g., Vemurafenib, Ipilimumab), have increased life expectancy by months, but resistance develops rapidly. The exact mechanism by which drug resistance develops is unclear; however, autophagy is known to play a major role. Autophagy is a self-degradative response of the cell towards nutrient stress. Conversely, autophagy also plays a housekeeping role by removing mis-folded or aggregated proteins and clearing damaged organelles by forming autophagosomes. Thus, autophagy is believed to play an important role in tumor progression and developing drug resistance during later stages of cancer. The Unfolded Protein Response (UPR) in the ER associated protein degradation is one of the pathways that initiates autophagy in stressed cells. UPR involves the activation of three signaling pathways mediated by IRE-1, PERK and ATF6. These pathways work towards decreasing the protein load of ER by increasing the expression of molecular chaperons, activation of ERAD (ER associated protein degradation) and autophagy. However if the damage caused by the stress is extensive UPR signaling pathways initiate apoptosis. Amy S. Lee, Cancer Res (2007); 77:3496-3499. Emerging evidence shows that in malignant cells ER stress can be pro-survival and contribute to the development of drug resistance by initiating autophagy.

Oncogenic BRAF is a known regulator of cellular metabolism that activates adaptive reprogramming through transcription factor microphthalmia-associated transcription factor (MITF) and co-factor PGC1α in melanoma cells. BRAF inhibition (BRAFi) is also known to promote mitochondrial respiration and increased cellular oxidative stress. Within this context, it is also known that BRAFi-resistant melanoma cells possess an adapted dependence on mitochondrial respiration (OXPHOS) and, consequently, an increased sensitivity to inhibitors of mitochondrial respiration. Further, this MAPKi shift in cellular metabolism towards OXPHOS and resulting increase in oxidative state has been implicated with an adapted-cellular program that actively maintains MAPKi-resistance. The relationship between cellular oxidative state and thiol (R(G)SH) redox equilibrium (ratio of reduced thiols to oxidized thiols) is well established. In the context of melanoma, the potential pivotal role in adaptation to BRAFi-induced oxidative stress is supported by emerging evidence that implicates phospholipid glutathione peroxidase 4 (GPX4) activity with melanoma.

The present inventors hypothesized that MAPKi driven changes in cellular thiol and (and GSH) metabolism play a key role in enabling cells to re-establish homeostasis and retain reproductive integrity (resistance) in the presence of growth inhibiting drugs (MAPKi). Therefore, the goal was to establish the role of reduced thiols in development of MAPKi resistance and simultaneously determine the clinical potential of targeting thiol redox equilibrium in combination with MAPKi to improve the efficacy of MAPKi to improve the efficacy of MAPKi in metastatic melanoma patients.

The invention relates to the administration of a GSH synthesis inhibitor to a cancer patient along with one or more anti-cancer compositions to increase the efficacy of the anti-cancer compositions by preventing drug resistance.

Definitions

As used herein, the term "GSH synthesis inhibitor" includes buthionine sulphoximine (BSO) and other compounds which inhibit the synthesis of glutathione, including salts, isomers, analogs, and derivatives of such compounds.

As used herein, the term "buthionine sulphoximine" or "BSO" includes salts, isomers, analogs, and derivatives of BSO. BSO effectively inhibits γ-glutamylcysteine synthetase by binding to the enzyme.

As used herein, the term "phenylbutyrate" includes salts, isomers, analogs and derivatives of phenylbutyrate. In certain embodiments, phenylbutyrate is Buphenyl® (sodium phenylbutyrate). Sodium phenylbutyrate is used for chronic management of urea cycle disorders (UCDs). Its mechanism of action involves the quick metabolization of sodium phenylbutyrate to phenylacetate. Phenylacetate then conjugates with glutamine (via acetylation) to form phenylacetylglutamine, and phenylacetylglutamine is excreted by the kidneys. It has been observed that sodium phenylbutyrate reduces Endoplasmic Reticulum (ER) stress.

The cellular response to ER stress is neither fully oncogenic nor completely tumor suppressive. It involves complex signaling with many pathways. The relative importance of each pathway varies between cells depending on chronicity of ER stress, and on relative expression of various associated proteins. As solid cancers grow, nutrients and oxygen required exceed capacity of existing vascular bed, which can trigger angiogenesis (development of new blood vessels) to get more oxygen/nutrients to the cancers. Cancers, however, usually become hypoxic and nutrient-depleted, and with the hypoxia leading to impaired generation of ATP. The low ATP levels compromise ER protein folding which leads to ER stress. Thus, unfolded, and/or misfolded proteins are associated with ER stress and cancer cells exist with higher levels of ER stress relative to health cells.

Potential outcomes as a consequence of ER stress include high rates of protein synthesis that would trigger increased expression of autophagy, which is cytoprotective during stress (liberates amino acids, and removes damaged organelles). Another outcome would be an increased tolerance to hypoxia, which would promote tumor growth. This would also increase autophagy, promoting drug resistance. Thus, a successful treatment would inhibit autophagy and promote cell death.

Sodium phenylbutyrate decreases ER Stress. Lowering ER stress prevents tolerance to hypoxia and prevents cytoprotective autophagy (which leads to drug resistance). Phenylbutyrate acts as a "chemical chaperone," meaning it guides proper protein folding, and the presence of properly folded proteins lowers ER stress.

As used herein, the term "anti-cancer agent" includes therapeutic agents that kill cancer cells; slow tumor growth and cancer cell proliferation; and ameliorate or prevent one or more of the symptoms of cancer. For example, the term "anti-cancer agent" includes vemurafenib and triphenylphosphonates (TPP). Vemurafenib (Zelboraf®) is a cancer growth blocker and is a treatment for advanced melanoma. Vemurafenib stops the proliferative effects of oncogenic BRAF protein. The standard method of administration is an oral tablet, administered 4× daily. Unfortunately, metastatic melanoma can resist vemurafenib treatment. Vemurafenib slows tumor progression for only about 5.3 months. As a result, finding an effective treatment for metastatic melanoma is challenging.

For example, the term "anti-cancer agent" includes a Triphenylphosphonium (TPP) agent or derivative thereof that increases reactive oxygen species (ROS) levels in cancer cell mitochondria, and a pharmaceutically acceptable diluent or carrier. As used herein, the term triphenylphosphonium (TPP) is any molecule containing a triphenylphosphine cation (+PPh$_3$) moiety. See, e.g., WO 2013/019975 and WO 2014/124384, which are incorporated by reference herein.

TPP salts can be reacted with alcohols, alkyl halides, and carboxylic acids, which allow them to be used as starting materials for the synthesis of a large variety of chemical derivatives, e.g., XTPP agents. Charged molecules generally cannot pass through cell membranes without the assistance of transporter proteins because of the large activation energies need to remove of associated water molecules. In the TPP molecules, however, the charge is distributed across the large lipophilic portion of the phosphonium ion, which significantly lowers this energy requirement, and allows the TPP to pass through lipid membranes. The phosphonium salts accumulate in mitochondria due to the relatively highly negative potential inside the mitochondrial matrix. The compositions of the present invention utilize XTPP agents that have activity in treating cancer cells, in that the XTPP agents preferentially localize to cancer cells, as compared to the comparable normal cells because cancer cells are often characterized by abnormal mitochondrial oxidative metabolism (Aykin-Burns N, Ahmad I M, Zhu Y, Oberley L W, and Spitz D R: Increased levels of superoxide and hydrogen peroxide mediate the differential susceptibility of cancer cells vs. normal cells to glucose deprivation. Biochem. J. 2009; 418:29-37. PMID: 189376440) and altered mitochondrial membrane potential (Chen L B: Mitochondrial membrane potential in living cells, Ann. Rev. Cell Biol. 1988; 4:155-81), relative to normal cells.

In certain embodiments, the TTP agent is 10-TTP or 12-TTP.

In certain embodiments, the anti-cancer agent is ipilimumab.

Compositions and Methods of Administration

The present invention provides a method for increasing the anticancer effects of a conventional cancer therapy (i.e., radio- and/or chemo-therapy) on cancerous cells in a mammal, comprising contacting the cancerous cell with an effective amount of a glutathione (GSH) synthesis inhibitor or a pharmaceutically acceptable salt thereof, and administering an additional conventional cancer therapy modality. In certain embodiments, the additional cancer therapy is chemotherapy and/or radiation. In certain embodiments, the GSH synthesis inhibitor or a pharmaceutically acceptable salt thereof and anti-cancer agent are administered sequentially to a mammal rather than in a single composition. In certain embodiments, the mammal is a human.

In certain embodiments of the methods described above, the composition does not significantly inhibit viability of comparable non-cancerous cells.

In certain embodiments of the methods described above, the cancer is breast cancer, prostate cancer, lung cancer, pancreas cancer, head and neck cancer, ovarian cancer, brain cancer, colon cancer, hepatic cancer, skin cancer, leukemia, melanoma, endometrial cancer, neuroendocrine tumors, carcinoids, neuroblastoma, glioma, tumors arising from the neural crest, lymphoma, myeloma, or other malignancies characterized by aberrant mitochondrial hydroperoxide metabolism. In certain embodiments, the cancer is the above cancers that are not curable or not responsive to other therapies. In certain embodiments, the cancer is a melanoma. In certain embodiments, the cancer is a glioma.

In certain embodiments of the methods described above, the tumor is reduced in volume by at least 10%. In certain embodiments, the tumor is reduced by any amount between 1-100%. In certain embodiments, the tumor uptake of molecular imaging agents, such as fluorine-18 deoxyglucose, fluorine-18 thymidine or other suitable molecular imaging agent is reduced by any amount between 1-100%. In certain embodiments, the imaging agent is fluorine-18 deoxyglucose, fluorine-18 thymidine or other suitable molecular imaging agent. In certain embodiments, the mammal's symptoms (such as flushing, nausea, fever, or other maladies associated with cancerous disease) are alleviated.

Administration of a compound as a pharmaceutically acceptable acid or base salt may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The GSH synthesis inhibitor and the anti-cancer agents can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard- or soft-shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

In one embodiment of the invention, the GSH synthesis inhibitor is BSO and is administered intravenously in a dosage of between about 1.5-17 g/m$^2$ as multiple infusion regimens.

The tablets, troches, pills, capsules, and the like may also contain the following: binders such as gum tragacanthin, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols, or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The dosage of the BSO or pharmaceutically acceptable salt thereof and the anti-cancer agent will vary depending on age, weight, and condition of the subject. Treatment may be initiated with small dosages containing less than optimal doses, and increased until a desired, or even an optimal effect under the circumstances, is reached. In general, the dosage, involves escalating doses of BSO, from 5 to 17 gm/m$^2$, as a multiple infusion regimen.

Higher or lower doses, however, are also contemplated and are, therefore, within the confines of this invention. A medical practitioner may prescribe a small dose and observe the effect on the subject's symptoms. Thereafter, he/she may increase the dose if suitable. In general, the BSO or pharmaceutically acceptable salt thereof and the anti-cancer agent are administered at a concentration that will afford effective results without causing any unduly harmful or deleterious side effects, and may be administered either as a single unit dose, or if desired in convenient subunits administered at suitable times.

A pharmaceutical composition of the invention is formulated to be compatible with its intended route of administration. For example, the therapeutic agent may be introduced directly into the cancer of interest via direct injection. Additionally, examples of routes of administration include oral, parenteral, e.g., intravenous, slow infusion, intradermal, subcutaneous, oral (e.g., ingestion or inhalation), transdermal (topical), transmucosal, and rectal administration. Such compositions typically comprise the BSO or pharmaceutically acceptable salt thereof and the anti-cancer agent and a pharmaceutically acceptable carrier. As used herein, "pharmaceutically acceptable carrier" is intended to include any and all solvents, dispersion media, coatings, antibacterial and anti-fungal agents, isotonic and absorption delaying agents, and the like, compatible with pharmaceutical administration, and a dietary food-based form. The use of such media and agents for pharmaceutically active substances is well known in the art and food as a vehicle for administration is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyethylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

It may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose or can be formulated in multiple dosage units. Treatment may require a one-time dose or may require repeated doses.

"Systemic delivery," as used herein, refers to delivery of an agent or composition that leads to a broad biodistribution of an active agent within an organism. Some techniques of administration can lead to the systemic delivery of certain agents, but not others. Systemic delivery means that a useful, preferably therapeutic, amount of an agent is exposed to most parts of the body. To obtain broad biodistribution generally requires a blood lifetime such that the agent is not rapidly degraded or cleared (such as by first pass organs (liver, lung, etc.) or by rapid, nonspecific cell binding) before reaching a disease site distal to the site of administration. Systemic delivery of lipid particles can be by any means known in the art including, for example, intravenous, subcutaneous, and intraperitoneal. In a preferred embodiment, systemic delivery of lipid particles is by intravenous delivery.

"Local delivery," as used herein, refers to delivery of an active agent directly to a target site within an organism. For example, an agent can be locally delivered by direct injection into a disease site, other target site, or a target organ such as the liver, heart, pancreas, kidney, and the like.

The term "mammal" refers to any mammalian species such as a human, mouse, rat, dog, cat, hamster, guinea pig, rabbit, livestock, and the like.

The terms "treat" and "treatment" refer to both therapeutic treatment and prophylactic or preventative measures, wherein the object is to prevent or decrease an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

In one embodiment of the invention, the GSH synthesis inhibitor is buthionine sulfoximine (BSO). However, any GSH synthesis inhibitor is appropriate for use in the invention. In one embodiment of the invention, the anti-cancer composition is a MAPK-pathway inhibitor (MAPKi) including, but not limited to, BRAF inhibitors (BRAFi), MEK inhibitors (MEKi), and ERK inhibitors (ERKi). Examples of BRAFi include, but are not limited to, vemurafenib, dabrafenib, and encorafenib. Examples of MEKi include, but are not limited to, refametinib, selumetinib, trametinib, and cobimetinib. Examples of ERKi include, but are not limited to, ERK1 and ERK2.

The GSH synthesis inhibitor may be administered concurrently with, prior to, or following administration of the one or more anti-cancer agents. In one embodiment, the GSH synthesis inhibitor may be administered up to 10 days in advance of administration of the one or more anti-cancer agents, or up to 10 days following the end of administration of the one or more anti-cancer agents. GSH synthesis inhibitors are typically administered intravenously (IV), but may also be administered by other conventional means of administration where applicable, such as orally, subcutaneously (SQ), intramuscularly (IM), nasally, buccally, etc.

MAPK pathway inhibition has significantly improved progression-free survival (PFS) and overall survival (OS) of patients whose metastatic melanoma malignancy is positive for specific mutations in the BRAF protein. However, durable responses are rare, with many patients experiencing dramatic initial responses to treatment (responsive phase) that is followed by subsequent acquisition of drug resistance over several months (resistant phase). In vitro, MAPK pathway inhibition, initially reduces survival of BRAF mutant melanoma cells by almost 70%. However, almost 30% of the cell population exhibits a resistant phenotype (survives MAPK pathway inhibition). Furthermore, with continuous treatment, the resistant phenotype becomes dominant. BRAF inhibition is known to shift cellular metabolism from glycolysis to mitochondrial respiration (OXPHOS). To refine our understanding of the timing of this metabolic shift, changes in metabolism and oxidative state of live BRAF$^{V600E}$ mutant melanoma cells (A375 and 451 Lu) were examined from the initiation of MAPKi treatments through the acquisition of resistance (approximately 30 days). In order to quantify the shift in metabolism, the ratio of basal metabolic oxygen consumption (BMOC) to extracellular acidification rate (ECAR, i.e., basal rate of glycolysis) by Seahorse SF6 extracellular flux analyzer was measured. Cells were treated (continuously) with BRAFi (vemurafenib, 5 µM) alone and in combination with MEKi (cobimetinib, 0.1 µM) and measurements were made using live cells at pre-determined time points. Continuous treatment of melanoma cells A375 and 451Lu with MAPKi (BRAFi alone and in combination with MEKi) resulted in an increase in BMOC/ECAR as cells approached the resistant phase. The observed shift in cellular metabolism with the onset of resistance correlates with significant changes in the mitochondrial and cellular oxidative state—suggesting a relationship between the onset of resistance and oxidative state of the cell. As cells became resistant to MAPKi, the fluorescence intensity of Mitosox and DHE oxidation decreased to baseline levels indicating re-establishment of new basal homeostasis and reproductive integrity. Considering the critical relationship between cellular oxidative state and intracellular glutathione redox buffering, the changes in amount of reduced GSH and the percent of GSH as GSSG were evaluated with continuous treatment of melanoma cells with MAPKi. We Continuous treatment of melanoma cells with MAPKi resulted in a steady and significant increase in the concentration of reduced GSH and a significant increase in the percent of total GSH as GSSG during the responsive phase, but that these values decreased as the melanoma cells acquired resistance to MAPKi.

To understand the role of thiol redox equilibrium in the development of melanoma MAPKi resistance involved pharmacologically disrupting the thiol (glutathione) redox balance in the presence of MAPKi. The effect of disrupting thiol redox equilibrium on development of MAPKi resistance was quantified in terms of clonogenic survival of cells when treated with BRAFi (vemurafenib, 5 µM) alone and in combination with thiol-reducing agent 2-Mercaptoethanol (ME, 150 µM) or glutathione synthesis inhibitor buthionine sulfoximine (BSO, 0.5 mM). Depletion of GSH using BSO in the presence of MAPKi prevented the development of resistance—i.e., the clonogenic survival of melanoma cells was dramatically and significantly reduced when treated with the MAPKi in combination with buthionine sulphoximine (BSO). On the contrary, combining BRAFi with a biochemically-enhanced source of reduced thiols (i.e., 2-mercaptoethanol; ME) boosted the development of resistance (higher clonogenic survival) in melanoma cells A375 and 451Lu. Similar effects were observed when A375 cells were treated with ME in combination with BRAFi+MEKi. Interestingly, the effect of depletion of reduced thiols (GSH) on acquisition of resistance was rescued by addition of ME to the BSO/MAPKi combination, indicating that reduced cellular thiols play a key and vital role in the development of melanoma resistance to MAPKi.

Figure 1B:
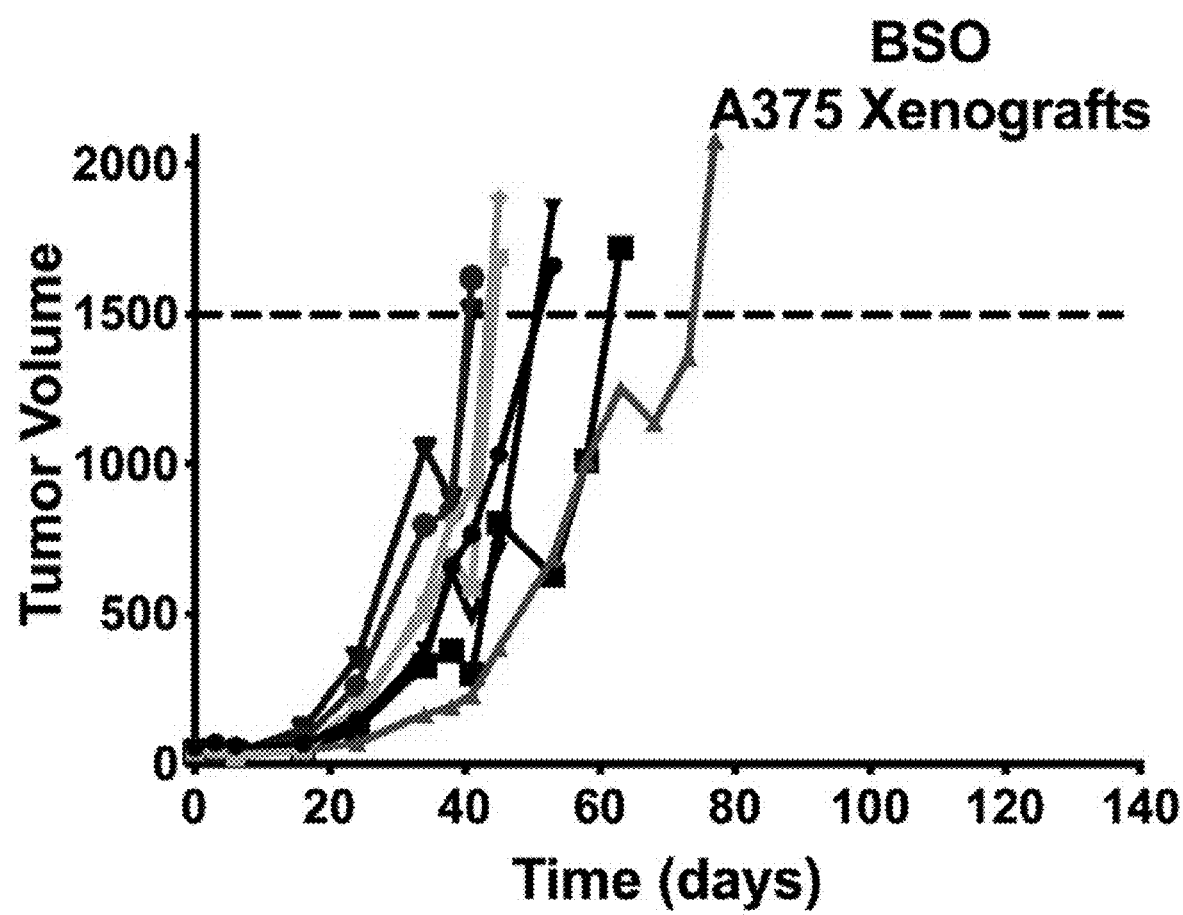
Figure 2:
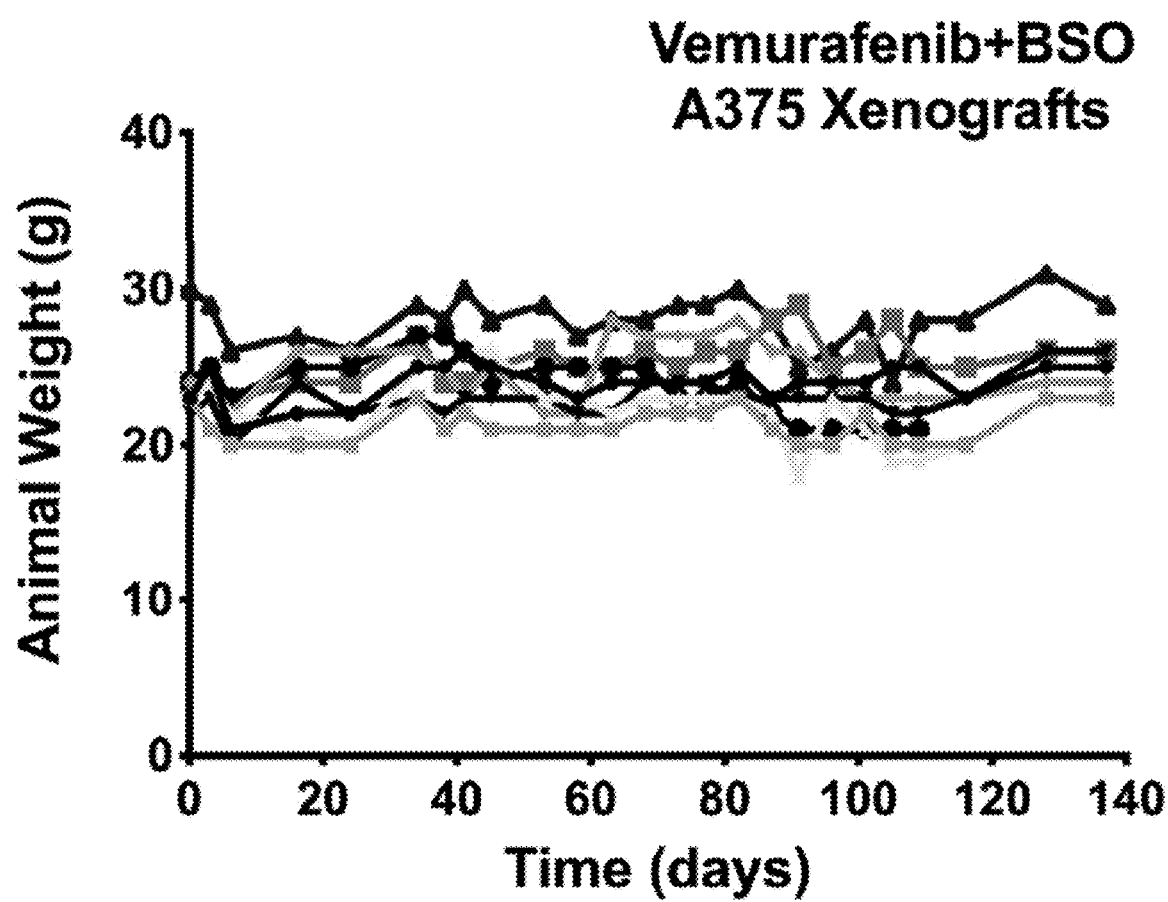
FIG. 2 illustrates that tumor xenografts in mice acquire resistance for BRAFi treatment alone within 140 days.
Figure 3:
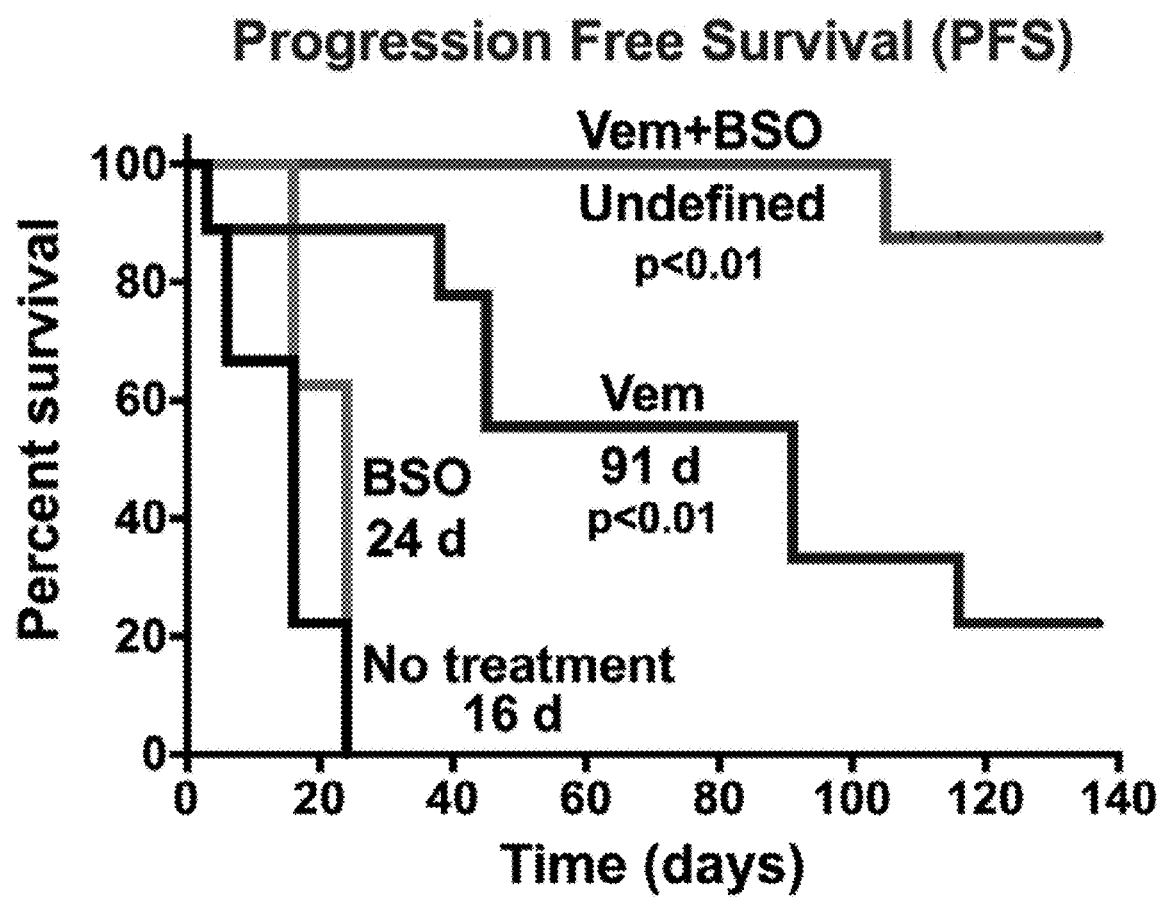
FIG. 3 illustrates that the combination of BSO with PLX4720 produces nearly 90% complete and durable tumor responses.
Figure 4:
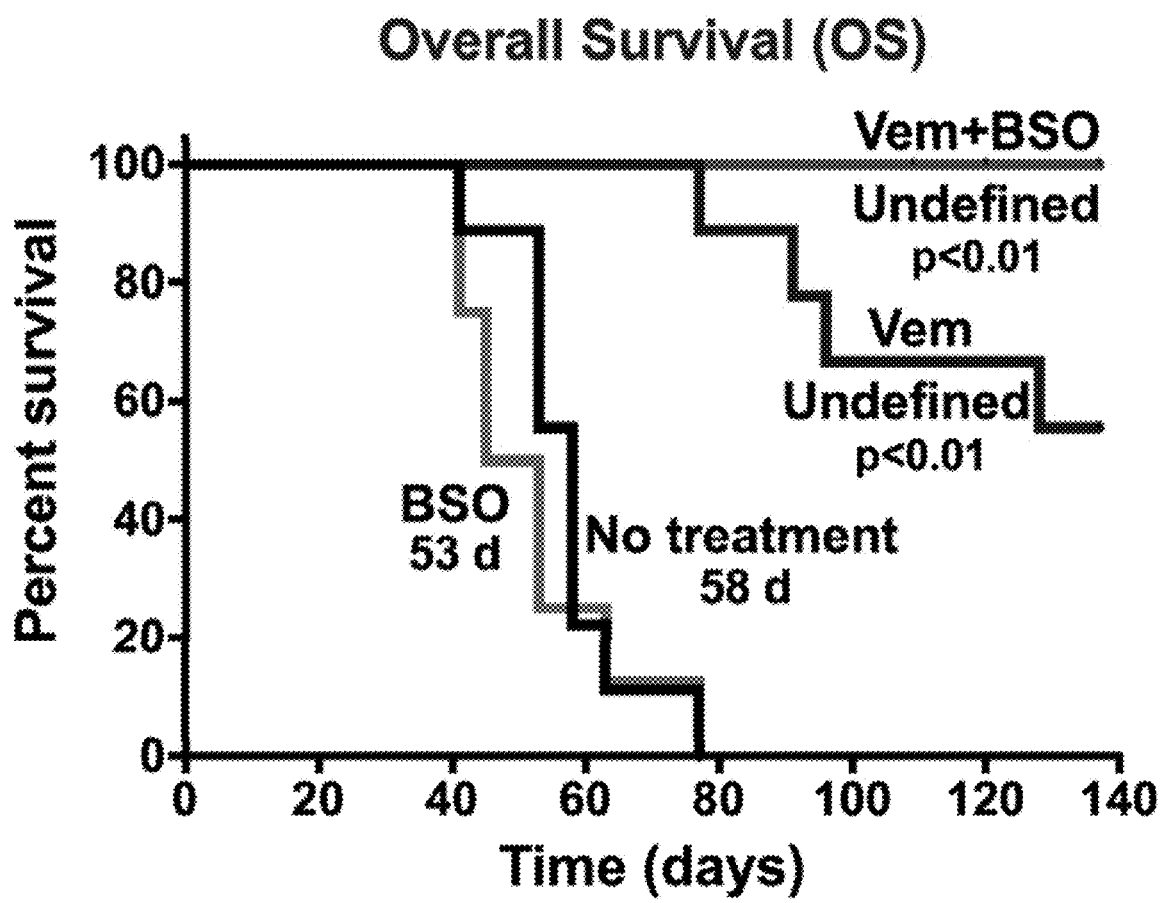
FIG. 4 illustrates that the complete response rate and overall survival (OS) for mice treated with the combination of BSO with PLX4720 was significantly higher than mice treated with BRAFi alone.

2-Mercaptoethanol is a reducing agent that leads to reduction of disulphide bonds to produce thiols. Therefore, treating cells (A375) with combination of BRAFi and ME increased the cellular concentration of GSH (reduced thiol), and treating cells with combination of BRAFi with BSO significantly decreased the cellular concentration of GSH to nearly undetectable levels. The effect of eliminating GSH in vivo was tested by treating mice (Athymic nu/nu) bearing A375 xenografts with rodent diet (AIN-76A) containing PLX4720 (vemurafenib, 416 mg/kg of diet) alone and in combination with BSO (15 mM in drinking water). No significant difference in tumor growth rate was observed for untreated controls (FIG. 1a) and mice treated with BSO alone (FIG. 1b). As expected, significantly lower GSH concentrations were observed in tumor samples collected from mice treated with BSO vs controls confirming the bioavailability of BSO in the tumor microenvironment. Tumor xenografts in mice treated with the AIN-76 diet mixed with PLX4720 were responsive initially, but approximately 80% of these tumors acquired resistance to BRAFi treatment alone within 140 days (i.e., 20% complete responses; FIG. 2). On the contrary, the combination of BSO with PLX4720 produced nearly 90% complete and durable tumor responses (FIG. 4). Body weight comparison between untreated control mice and mice treated with combination of BRAFi and BSO indicated that the combination was well tolerated. Tumor progression was defined as a 50% increase (approximately a two standard deviation increase) in tumor volume from study initiation. Therefore, progression free survival (PFS) of mice treated with the combination of PLX4720 (vem, BRAFi) and BSO was significantly higher than mice treated with BRAFi alone (FIG. 3). In addition, the complete response rate and overall survival (OS) for the cohort treated with the combination was strikingly and significantly higher compared to untreated and PLX4720 treated groups (FIG. 4).

The following examples are offered to illustrate but not limit the invention. Thus, it is presented with the understanding that various formulation modifications as well as method of delivery modifications may be made and still are within the spirit of the invention.

Example 1

Methods

Cell Culture and Adenovirus Transfection

BRAF-mutant (BRAF$^{V600E}$) melanoma cell line A375 was purchased from ATCC. BRAF$^{V600E}$ metastatic melanoma cell line 451Lu and its vemurafenib-resistant derivative 451LuBR were obtained from the Wistar Special Collection. A375 and 451Lu cells were cultured in high glucose DMEM (Gibco) supplemented with 10% FBS (Gibco) and 1% Penstrep. 451LuBR cells were cultured in high glucose DMEM supplemented with 10% FBS, 1% Penstrep, and 5 µM vemurafenib (Selleckchem). A375-CG-LC3B cells were obtained using a retroviral vector containing a coding sequence for a mCherry-EGFP-LC3B tandem protein (pBABE-puro mCherry-EGFP-LC3B, #22418, Addgene). The retrovirus was packaged in GP2-293 cells by co-transfection of 1 µg of viral DNA constructs and 1 µg of envelope plasmid (pVSV-G) in 20 µL PolyFect transfection reagent (Qiagen) for 48 hours at 37° C., 5% $CO_2$. Virus-rich media was collected, aliquoted, and stored at −80° C. Cells were infected using the virus-rich media in DMEM (high glucose) for 12 h followed by incubation in complete media (high-glucose DMEM with 10% FBS) for 24 h. Infected cells were selected using 2 µg mL$^{-1}$ puromycin and transfection was confirmed using microscopy and flow cytometry. A375-CG-LC3B cells were maintained in high glucose DMEM (Gibco) supplemented with 10% FBS (Gibco) and 1% Penstrep and 1 µg mL$^{-1}$ puromycin. All the cell lines were maintained in 5% $CO_2$ at 37° C.

Drug Treatment

A375 and 451Lu cells were treated MAPK-pathway inhibitors (MAPKi), BRAF$^{V600E}$ inhibitor (BRAFi) vemurafenib (Vem, 5 µM, Selleckchem) alone and in combination with MEK inhibitor (MEKi) cobimetinib (Cobi, 0.1 µM, Selleckchem) for up to 35 days (4, 6, 10, 14, 21,2 8 and 35 day time points). Buthionine sulfoximine (BSO, 0.5 mM, Sigma-Aldrich) was used to inhibit glutathione (GSH) synthesis in the cells. Cells were treated with β-mercaptoethanol (ME, 150 µM, Sigma-Aldrich). Further, to attenuate ER-stress, cells were treated with sodium 4-phenylbutyrate (PBA, 2 mM, Sigma-Aldrich). Cells were treated with Hydroxychloroquine (HCQ, 12 µM, Selleckchem) to inhibit autophagic flux. Dimethyl sulfoximine (DMSO) and PBS were used as vehicle controls.

In Vitro Survival Assays

Clonogenic assays were conducted to quantify changes in the reproductive integrity of cells under experimental conditions described herein. Cells were treated at 60-70% confluency with suitable vehicle controls and experimental treatments. Total cell pool (floaters and adherent cells) were collected at pre-determined time points. Cells from the total cell pool were re-plated at single cell density in 60 mm dishes (Corning, tissue culture treated) in triplicates. The colonies were allowed to form over 10-14 days. Once visible colonies appeared, they were fixed, stained and counted to obtain the plating efficiency.

To obtain the percent live, non-apoptotic cells (survival percent), cells were plated in six-well dishes (80,000-100,000 cells well$^{-1}$). The plates were treated in triplicate when the wells reached 60-80% confluency. The total cell pool was collected and centrifuged (1200 rpm for 5 min). The cell pellets were washed twice with room temperature DPBS. The washed cell pellet was re-suspended in Annexin V buffer (556454, BD Biosciences) and incubated with Annexin V Allophycocyanin (APC)-conjugated antibody, 1:250 (A35110, Thermo Fisher) and Hoechst 33258 pentahydrate (4 µg mL$^{-1}$, Molecular Probes) for 10 min at room temperature. Samples were analyzed (50,000 events) using LSR II flow cytometer (Becton-Dickson). The flow readout was used to calculate the survival percent using Flow Jo software (V10.4).

Autophagic Flux

Autophagy was quantified as autophagic flux ($A_f$) using A375-CG-LC3B cells using the formula:

$$A_f = F_{mcherry}/F_{GFP}$$

where $F_{mcherry}$ is mcherry fluorescence measured using the 532 nm laser and $F_{GFP}$ is GFP fluorescence measured using the 488 nm laser on LSR II. 60-80% confluent six-well plates were treated in triplicates with suitable vehicle controls or experimental treatments. At pre-determined time points the total cell pool was collected, centrifuged (1200 rpm, 5 min), and washed (twice) with cold PBS. The cell pellets were stained with apoptotic marker Annexin V and Hoechst 33258 as described above. Samples were analyzed on an LSR II flow cytometer (BD). $A_f$ was calculated for live, non-apoptotic (Hoechst negative, Annexin V negative) population using the derived parameter function in Flow Jo software (V10.4).

Transmission Electron Microscopy (TEM)

Transmission electron microscopy (TEM) is considered an accurate method for the detection and quantification of autophagy. The high resolution of TEM was used to accurately quantify autophagy by quantifying the area covered by autophagosomes (AFA). To quantify AFA, cells were cultured and appropriately treated in 60 mm dishes. 70-80% confluent dishes were fixed overnight with 2.5% glutaraldehyde in 0.1 M cacodylate buffer followed by rinsing in 0.1 M cacodylate buffer. Dishes were treated with a buffered 1% osmium tetroxide solution reduced with 1.5% potassium ferrocyanide for 30 min at room temperature post fixation followed by a second wash with 0.1 M cacodylate buffer. The cells were then stained en bloc with 2.5% uranyl acetate. The staining was followed with a complete dehydration using gradually increasing concentrations of ethanol to 100%. Infiltration of Eponate 12 epoxy resin and ethanol was performed for 1 hour at a 1:1 concentration followed by several changes of 100% resin. The dish was cured for 48 hours at 60 degree Celsius. A 5 mm×5 mm square grid was placed in the dish to transpose the lines onto the back of the cured dish. The squares on the grid were numbered beginning from the upper right-hand corner. The total number of squares on the dish was counted and divided by four. Four random squares were chosen using a random number generator chart. Selected squares were collected and en-face sections of 80 nm thickness were cut using a Leica UC-6 ultramicrotome, that were collected on 75 mesh copper grids coated with a thin layer of formvar for stability. The grids were then counterstained with 5% uranyl acetate for 2 minutes and Reynold's lead citrate for 2 minutes. Samples were imaged using a JEOL 1230 transmission electron microscope at 120 kV. Eight cells per section were imaged based on pre-determined criteria and magnification. Stereology to obtain the AFA was accomplished using Area Fraction-Fractionator (this instrument was purchased with an NIH Shared Instrumentation Grant #1S10 OD014165-01A1). A 7 µm×7 µm counting frame with a grid spacing of 0.5 µm was used. The area covered by autophagosomes was differentiated from the total cell area by using different probes. The data was plotted as AFA in treated group normalized to untreated control groups.

Intra-Cellular Glutathione Levels

Cells were plated (300,000) in 100 mm dishes (Corning, Tissue culture treated). 60-70% confluent dishes were treated with suitable vehicle controls or experimental treatments. The cells were washed with PBS and scraped in 100-200 µL of 5% 5-sulphosalicyclic acid (Sigma Aldrich). The samples were centrifuged at 5000 rpm for 5 min to precipitate protein. The supernatant was used to measure the total cellular glutathione (GSH) by applying the 5,5'-dithiobis-2-nitrobenzoic acid (DTNB) recycling assay in which the rate at which the yellow color accumulates with the introduction of DTNB is proportional to the amount of total glutathione (GSH (reduced)+GSSG (oxidized)) present measured by spectrophotometry (Beckman 800 spectrophotometer). Glutathione disulfide (GSSG) was measured by adding 20 µl of a 1:1 mixture of 2-vinylpyridine and ethanol per 100 µl of sample and incubating for 2 h prior to assaying. The precipitated protein was re-suspended in 0.1 N NaOH, and protein levels determined using the BCA Assay Kit (Thermo Scientific). Glutathione determinations were normalized to protein content of whole homogenates.

In-Vivo Studies: Athymic Nu/Nu Mouse Model

Female athymic nu/nu mice (age six weeks) were purchased from Envigo (previously Harlan Laboratories) and housed in the Animal Care Facility at The University of Iowa (Iowa City, Iowa). All procedures were approved by The University of Iowa Institutional Animal Care and Use Committee. All mice were naïve to treatments at the time of xenograft. For each xenograft, 1-3×$10^6$ cells (451LuBR and A375) were implanted subcutaneously in a 1:1 suspension of Matrigel (Corning) and PBS (flank) using a 27-gauge needle. For all in vivo studies, the mice were randomly assigned to experimental groups post-implant. Animals developed tumors within 7-10 days post-implant. Initiation of treatments was standardized to the time that tumor volume ([(longest length)×(smallest length^2)]/2) reached 80-100 mm$^3$. The dose and mode of delivery for the drugs used is shown in Table 1:

TABLE 1

Mode of delivery for the drugs used.

| Drugs | Mode of delivery |
|---|---|
| BSO | Drinking Water |
| PLX4720 (vemurafenib, BRAFi) | AIN-76A rodent diet |
| Vemurafenib | PO (Orally) |
| Cobimetinib | PO |
| Hydroxychloroquine (HCQ) | PO |
| 4-phenylbutyrate (PBA) | Intraperitoneal (IP) |

Figure 5:
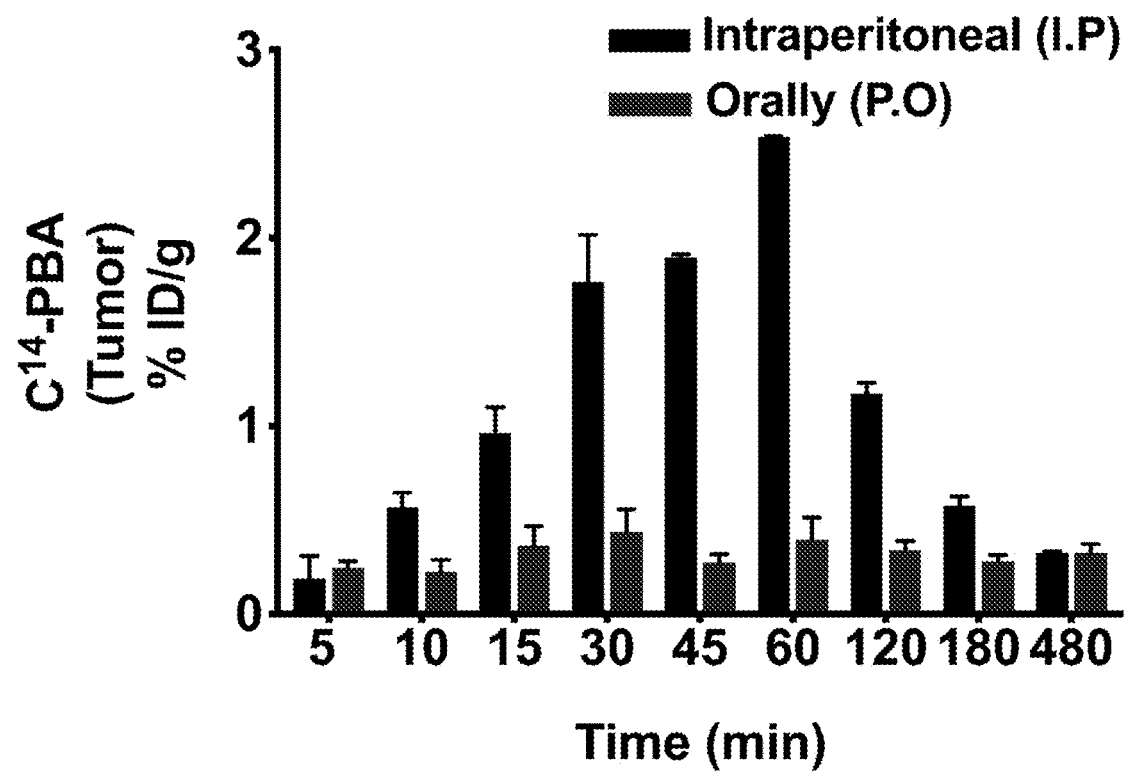
FIG. 5 illustrates the pharmacokinetics B-14 labeled PBA in mice. Biodistribution of C14-PBA in 451LuBR tumor (N=2).

The dose and mode of delivery for PBA was determined by analyzing the pharmacokinetics C-14 labeled PBA in mice (FIG. 5). These drugs were administered alone and in combination depending on the experimental group. The mice were monitored for their state of health every day. Tumor volume and animal weights were measured twice per week. Mice were euthanized when the observed state of health reached the endpoint according to the approved IACUC protocol or when the tumor volume reached 1500 mm$^3$.

Statistics was conducted using the tumor sizes (mm$^3$) that were obtained periodically throughout the experiments, resulting in repeated measurements for each mouse. Linear mixed effects regression models were used to estimate and compare treatment group-specific tumor growth curves. Pairwise comparisons were performed to identify treatment group differences in the growth curves. The Kaplan-Meier method was used to estimate the survival curves, and group comparisons were made using the log rank test. Mice who developed ulcerations were censored at day of euthanasia. All tests were two-sided and carried out at the 5% significance level using SAS v9.4 (SAS Institute, Cary, N.C.).

Immunohistochemistry Staining for LC3B Protein Expression

Tumor tissue was collected from mice at day 60 (posthumously). The paraffin embedded tumor tissue was cut into 5 µm sections. The sections were deparaffinized and rehydrated using the autostainer. Antigen retrieval was done in 10 mM citrate buffer (95° C., 650 watts). Membrane permeabilization was done using 0.1% Triton-X in PBS (10 min, room temperature). Hydrogen peroxide reductase was quenched by incubating the slides in 3% hydrogen peroxide ($H_2O_2$) (15 min at room temperature). Sections were incubated in 5% normal goat serum in PBS (pH 7.4) for 2 h at room temperature. Next, sections were incubated with primary LC3 antibody (1:100, Rabbit-anti-LC3B (D11) XP antibody, Cell Signaling Technology (3868)) at 4° C. overnight. Post primary antibody incubation, slides were washed with PBS (pH 7.4) (3×5 min). The tissue sections were incubated with ImmPRESS anti-rabbit-H1RP conjugate secondary antibody (Vector Laboratory) (30 min at room temperature). Sections were washed as mentioned above; incubated with ImmPACT NovaRED kit (SK4805, Vector laboratories) chromogen. The chromogen solution was removed as soon as the brown color was visible (~2 min). Slides were washed in running distilled water for 10 min and counterstained with Harris hematoxylin (15 s). Slides were washed in distilled water (10 min). Lastly, the slides were dehydrated and mounted with Clear Permaslip and cover glass. The LC3B expression was imaged and quantified using a Leica Ariol Slide Scanner.

Mitochondrial Oxygen Consumption & Extracellular Acidification Rate

Mitochondrial oxygen consumption rate (OCR) and Extracellular Acidification Rate (rate of glycolysis; ECAR) were measured using a Seahorse XF96 flux analyzer system (Agilent). Cells were seeded in 96-well Seahorse XF96 cell culture microplates (10,000-15,000 cells well$^{-1}$) and treated at 60-70% confluency. At pre-determined time points, cells were washed, followed by 1 h incubation in pre-warmed Seahorse Bioscience modified DMEM XF assay medium supplemented with 25 mM glucose and 1 mM sodium pyruvate. OCR and ECAR were measured in real time by Seahorse Bioscience XF96 extracellular flux analyzer. Cell number in individual wells was obtained using a standard hemocytometer. The rates were normalized to a per cell basis for every time point (amol $O_2$ cell$^{-1}$ s$^{-1}$).

Intra-Cellular Oxidative State by Flow Cytometry

The intra-cellular oxidative state was quantified using a redox-sensitive fluorescent probe, Dihydroethidium (DHE). In the presence of reactive oxygen species (ROS), DHE is oxidized to form ethidium cations; 2-hydroxyethidium or ethidium (depending on the type of ROS), both of which can be detected at the excitation/emission maxima of 518/606 nm[40]. Cells were plated in 6-well plates (80,000 cells well$^{-1}$; 60-70% confluent wells; in triplicate). Cells were stained at specific time points with DHE according to the manufacturer's protocol (D1168, Thermo Fisher Scientific). Briefly, treated cells were harvested; washed with PBS containing 5 mM sodium pyruvate; and centrifuged at 1200 rpm for 5 min. The cell pellets were resuspended and incubated in 500 µL of 10 µM DHE in PBS (containing 5 mM sodium pyruvate) for 40 min at 37° C., in the dark. Subsequently, the samples were filtered through a 35 μm mesh filter into polystyrene 12×75 mm test tubes (352052, Falcon) and placed on ice. Hoechst 33342 was used as a live-dead discriminator. Cells treated with Antimycin A (10 μM) were used as experimental positive controls. The samples were analyzed on an LSR II flow cytometer (Becton-Dickson). Fluorescence intensity was recorded for 10,000 Hoechst negative events and the Median Fluorescence Intensity (MFI) was quantified using FlowJo software (V10.4). Data for treated groups was normalized to untreated control cells and plotted as normalized median fluorescence intensity (NMFI).

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A combination of a glutathione (GSH) synthesis inhibitor and an anti-cancer composition comprising vemurafenib, whereby the GSH synthesis inhibitor is included in a dosage of from 1.5-17 g/m$^2$ buthionine sulphoximine (BSO).

2. The combination of claim 1, wherein the GSH synthesis inhibitor is administered simultaneously with the anti-cancer composition.

3. The combination of claim 1, wherein the GSH synthesis inhibitor and the anti-cancer composition are administered sequentially.

4. The combination of claim 1, wherein administration of the anti-cancer composition begins about 1 to about 10 days before administration of the GSH synthesis inhibitor.

5. The combination of claim 1, wherein administration of the GSH synthesis inhibitor begins about 1 to about 10 days before administration of the anti-cancer composition.

6. The combination of claim 1, wherein administration of the GSH synthesis inhibitor and administration of the anti-cancer composition begin on the same day.

7. The combination of claim 1, wherein the anti-cancer composition further comprises cobimetinib.

8. The combination of claim 1, wherein the anti-cancer composition comprises a derivative of triphenylphosphonium (TPP).

9. The combination of claim 1, wherein the anti-cancer composition comprises ipilimumab.

10. A kit comprising a GSH synthesis inhibitor, a container, and a package insert or label indicating the administration of the GSH synthesis inhibitor with an anti-cancer composition for treating melanoma, whereby the GSH synthesis inhibitor is buthionine sulphoximine (BSO) in a dosage of from 1.5-17 g/m$^2$, and further providing that the anti-cancer composition comprises vemurafenib.

11. A method for treating a drug-resistant melanoma in a mammal, comprising administering to the mammal that is resistant to MAPK pathway inhibitor and/or could acquire resistance to MAPK pathway inhibitors a combination of a GSH synthesis inhibitor and vemurafenib, whereby the GSH synthesis inhibitor and the vemurafenib are administered sequentially, and further providing that the GSH synthesis inhibitor comprises buthionine sulphoximine (BSO) in a dosage of from 1.5-17 g/m$^2$.

12. The method of claim 11 whereby the BSO is administered 1-10 days prior to the vemurafenib.

13. The method of claim 11 whereby the vemurafenib is administered 1-10 days prior to the BSO.

14. A method for treating a drug-resistant melanoma in a mammal, comprising administering to the mammal that is resistant to MAPK pathway inhibitor and/or could acquire resistance to MAPK pathway inhibitors a combination of buthionine sulphoximine (BSO) and vemurafenib, and further providing that the BSO is administered in a dosage of from 1.5-17 g/m2.

* * * * *